(12) United States Patent
Goodwin

(10) Patent No.: US 6,640,625 B1
(45) Date of Patent: Nov. 4, 2003

(54) METHOD AND APPARATUS FOR MEASURING FLUID DENSITY DOWNHOLE

(76) Inventor: Anthony R. H. Goodwin, 599 High St. Ext., Thomaston, CT (US) 06787-1212

( * ) Notice: Subject to any disclaimer, the term of this patent is extended or adjusted under 35 U.S.C. 154(b) by 0 days.

(21) Appl. No.: 10/140,670

(22) Filed: May 8, 2002

(51) Int. Cl.[7] ............................................. E21B 49/00
(52) U.S. Cl. ...................... 73/152.05; 73/61.75; 73/597
(58) Field of Search ...................... 73/152.05, 152.55, 73/152.01, 152.16, 152.18, 152.19, 152.22, 152.58, 53.01, 61.75, 599, 602, 597, 861.29; 175/58; 600/468

(56) References Cited

U.S. PATENT DOCUMENTS

| | | | |
|---|---|---|---|
| 3,780,575 A | 12/1973 | Urbanosky | 73/152 |
| 3,811,321 A | 5/1974 | Urbanosky | 73/155 |
| 3,813,936 A | 6/1974 | Urbanosky et al. | 73/155 |
| 3,859,851 A | 1/1975 | Urbanosky | 73/155 |
| 4,994,671 A | 2/1991 | Safinya et al. | 250/255 |
| 5,167,149 A | 12/1992 | Mullins et al. | 73/155 |
| 5,201,220 A | 4/1993 | Mullins et al. | 73/155 |
| 5,266,800 A | 11/1993 | Mullins | 250/256 |
| 5,509,299 A * | 4/1996 | Sarvazjan et al. | 73/64.53 |
| 5,741,962 A * | 4/1998 | Birchak et al. | 73/152.16 |
| 5,859,430 A | 1/1999 | Mullins et al. | 250/255 |
| 5,932,793 A * | 8/1999 | Dayton et al. | 73/24.05 |
| 5,939,717 A | 8/1999 | Mullins | 250/255 |
| 6,202,494 B1 * | 3/2001 | Riebel et al. | 73/861.29 |
| 6,279,385 B1 * | 8/2001 | Krawetz et al. | 73/53.01 |
| 6,343,507 B1 * | 2/2002 | Felling et al. | 73/152.19 |
| 6,401,538 B1 * | 6/2002 | Han et al. | 73/599 |
| 6,457,539 B1 * | 10/2002 | Skinner | 175/58 |
| 6,474,152 B1 * | 11/2002 | Mullins et al. | 73/152.22 |
| 6,485,427 B1 * | 11/2002 | Lee et al. | 600/468 |
| 6,487,894 B1 * | 12/2002 | Dukhin et al. | 73/61.75 |
| 6,490,916 B1 * | 12/2002 | Goodwin et al. | 73/152.58 |

OTHER PUBLICATIONS

Riazi et al, Use of the Velocity of Sound in Predicting the PVT Relations, 1992, Fluid Phase Equilabria, 90 (1993)251–264 Elsevier. Lecture 18, unknown, Feb. 11, 2003.*
Lecture 18, unknown, Feb. 11, 2003.*
Anderson, Speed of Sound: Heat Capacity Ratio ($C_p/C_v$) of Gases, unknown, 1999.*
Yvas et al, Excess Molar Volumes and Isentropic Compressibilities of Binary Liquid Mixtures Containing . . . , Oct. 2002, Pramana, Indian Academy of Sciences, 59, 4, 10/02, 663–670.*
Drakos, Compressibility, 1997, www.phys.virginia.edu/classes/311/notes/coompflu2/node4.html. Salzman, Adiabatic Compressibility, Feb. 15, 2001.*
Salzman, Adiabatic Compressibility, Feb. 15, 2001.*
Mullins, O. C. et al. "Effects of High Pressure on the Optical Detection of Gas by Index–of–Refraction Methods". Applied Optics (Dec. 1994), vol. 33, No. 34, pp. 7963–7970.

* cited by examiner

*Primary Examiner*—Hezron Williams
*Assistant Examiner*—Jay Politzer
(74) *Attorney, Agent, or Firm*—David P. Gordon; William B. Batzer; John J. Ryberg

(57) ABSTRACT

Apparatus for determining the density of a fluid downhole includes apparatus for measuring compressibility of the fluid and apparatus for determining the speed of sound through the fluid. According to the methods of the invention, density of the fluid is calculated based upon the relationship between density, compressibility, and the speed of sound through the fluid.

18 Claims, 5 Drawing Sheets

METHOD AND APPARATUS FOR MEASURING FLUID DENSITY DOWNHOLE

This application is related to co-owned U.S. patent application Ser. No. 09/704,630 filed Nov. 2, 2000, entitled "Methods and Apparatus for Optically Measuring Fluid Compressibility Downhole", now issued as U.S. Pat. No. 6,474,152, the complete disclosure of which is hereby incorporated herein by referenced.

BACKGROUND OF THE INVENTION

1. Field of the Invention

The present invention relates to the analysis of downhole hydrocarbon fluids. More particularly, the present invention relates to apparatus and methods for the in situ determination of the density of hydrocarbon fluids in a geological formation.

2. State of the Art

Naturally occurring hydrocarbon fluids include a wide range of fluids including dry natural gas, wet gas, condensate, light oil, black oil, heavy oil, and heavy viscous tar. The physical properties of these various hydrocarbon fluids, such as density, viscosity, and compressibility vary considerably. In addition, the separation of each of the hydrocarbon fluid compositions into distinctly separate gas, liquid and solid phases, each with its own physical properties, occurs at certain contours of pressure and temperature within the formation. This is referred to generally as the "phase behavior" of the hydrocarbon.

The economic value of a hydrocarbon reserve, the method of production, the efficiency of recovery, the design of production hardware systems, etc., all depend upon the physical properties and phase behavior of the reservoir hydrocarbon fluid. Hence, it is important that the fluid properties and phase behavior of the hydrocarbon be determined accurately following the discovery of the hydrocarbon reservoir, so that a decision of whether it is economically viable to develop the reservoir can be made; and if viable, an appropriate design and plan for the development of the reservoir can be adopted. With that in mind, those skilled in the art will appreciate that the ability to conduct an analysis of formation fluids downhole (in situ) is extremely desirable.

The assignee of this application has provided a commercially successful borehole tool, the MDT (a trademark of Schlumberger) which analyzes formation fluids in situ. The MDT extracts and analyzes a flow stream of fluid from a formation in a manner substantially as set forth in co-owned U.S. Pat. Nos. 3,859,851 and 3,780,575 to Urbanosky which are hereby incorporated by reference herein in their entireties. The OFA (a trademark of Schlumberger), which is a module of the MDT, determines the identity of the fluids in the MDT flow stream and quantifies the oil and water based on other co-owned technology. In particular, co-owned U.S. Pat. No. 4,994,671 to Safinya et al. provides a borehole apparatus which includes a testing chamber, means for directing a sample of fluid into the chamber, a light source preferably emitting near infrared rays and visible light, a spectral detector, a data base means, and a processing means. Fluids drawn from the formation into the testing chamber are analyzed by directing the light at the fluids, detecting the spectrum of the transmitted and/or backscattered light, and processing the information accordingly in order to quantify the amount of water and oil in the fluid. As set forth in co-owned U.S. Pat. No. 5,266,800 to Mullins, by monitoring the optical absorption spectrum of the fluid samples obtained over time, a determination can be made as to when a formation oil is being obtained as opposed to a mud filtrate. Thus, the formation oil can be properly analyzed and quantified by type.

The Safinya et al., and Mullins patents represent great advances in downhole fluid analysis, and are particularly useful in the analysis of oils and water present in the formation. The issues of in situ gas quantification and analysis are addressed in the co-owned U.S. Pat. No. 5,167,149 to Mullins et al., U.S. Pat. No. 5,201,220 to Mullins et al., U.S. Pat. No. 5,859,430 to Mullins et al., U.S. Pat. No. 5,939,717 to Mullins, and in O. C. Mullins et al., "Effects of high pressure on the optical detection of gas by index-of-refraction methods", Applied Optics, Vol. 33, No. 34, pp. 7963–7970 (Dec. 1, 1994). In particular, U.S. Pat. No. 5,859,430 to Mullins et al. discloses a method and apparatus for the downhole compositional analysis of formation gases which utilizes a flow diverter and spectrographic analysis. More particularly, the apparatus includes diverter means for diverting formation gas into a separate stream, and a separate gas analysis module for analyzing the formation gas in that stream. The methods and apparatus are useful in determining what types of gas are present in the formation fluid. U.S. Pat. No. 5,939,717 to Mullins, on the other hand, is directed to methods and apparatus for determining in situ gas-oil ratios (GOR) which are necessary for establishing the size and type of production facilities required for processing newly discovered oil.

Despite these large advances in downhole analysis and quantification of oil, gas, and water, and gas-oil ratios, additional information regarding physical properties of the hydrocarbons such as the hydrocarbon compressibility and density are desired. Previously incorporated Ser. No. 09/704,630 discloses methods and apparatus for optically measuring fluid compressibility downhole. The compressibility of a formation hydrocarbon sample is determined downhole by using a borehole tool to obtain the sample downhole, and, at two different pressures, subjecting the sample to near infrared illumination and conducting spectral absorption measurement of peaks at and/or around about 6,000 cm$^{-1}$ and/or at and/or about 5,800 cm$^{-1}$ (the absorption peaks of methane and crude oil respectively). The compressibility of the sample is determined from the change in the peak areas, the change in pressure, and the measured peak area itself. According to a preferred embodiment of the invention, the pressure is changed at least 2000 pounds per square inch (psi), and preferably 4000 or more psi between measurements.

Fluid density measurement normally requires the measurement of the volume occupied by a known mass or the measurement of the mass of a known volume. Density can be determined in a laboratory by analyzing a fluid sample taken downhole from the formation. These measurements are time consuming and suffer from systematic errors that arise from irreversible changes in the sample upon transportation from downhole to the laboratory. These measurements also assume that a representative sample was obtained by the sampling tool. Although these measurements could be performed at the well head, thereby reducing the time required for an identification of low quality samples, such measurements would still be subject to the issues of sample changes that might occur while the sample is brought from downhole to the surface.

SUMMARY OF THE INVENTION

It is therefore an object of the invention to provide methods and apparatus for measuring fluid density downhole.

It is also an object of the invention to provide methods and apparatus for measuring fluid density downhole with a sampling device during investigative logging.

It is another object of the invention to provide methods and apparatus for measuring fluid density downhole with permanent sensors during production logging.

It is still another object of the invention to provide methods and apparatus for measuring fluid density downhole of both stagnant fluid and flowing fluid.

In accord with these objects which will be discussed in detail below, the methods of the present invention include measuring the compressibility of fluid using the methods and Optical Fluid Analyzer apparatus of the previously incorporated co-owned application, measuring the speed of sound in the downhole fluid, and calculating fluid density based on the compressibility of the fluid and the speed of sound through the fluid. The apparatus of the invention includes at least one sound transceiver and a signal processor. Prior to or after the compressibility of the fluid is obtained, sound is transmitted through the fluid and reflected back to the sound transceiver over a known distance. The signal processor calculates the time delay between the transmission and reception, and, using the known distance, calculates the speed of sound through the fluid. The speed of sound is then used with the compressibility of the fluid to determine density based on a known physical relationship between isentropic compressibility, speed of sound and density.

The sound transceiver is preferably mounted within the tubing of the Optical Fluid Analyzer so that compressibility and speed of sound measurements can be made on the same sample.

According to another embodiment of the apparatus of the invention, two sound transceivers are used so that the speed of sound can be measured in two opposite directions through the fluid. This allows the measurement of the flow rate of flowing fluid as well as the speed of sound through the fluid. Off the shelf ultrasonic "time of flight" flow meters may be adapted to suit the methods of the invention. These devices typically utilize quartz transducers and generate sound pulses in the range of ten micro seconds to one millisecond with a frequency in the range of 100 KHz to one MHz.

Alternate embodiments of the invention contemplate permanent or semi-permanent installations of sensors so that the density of the formation fluids may be measured during production.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
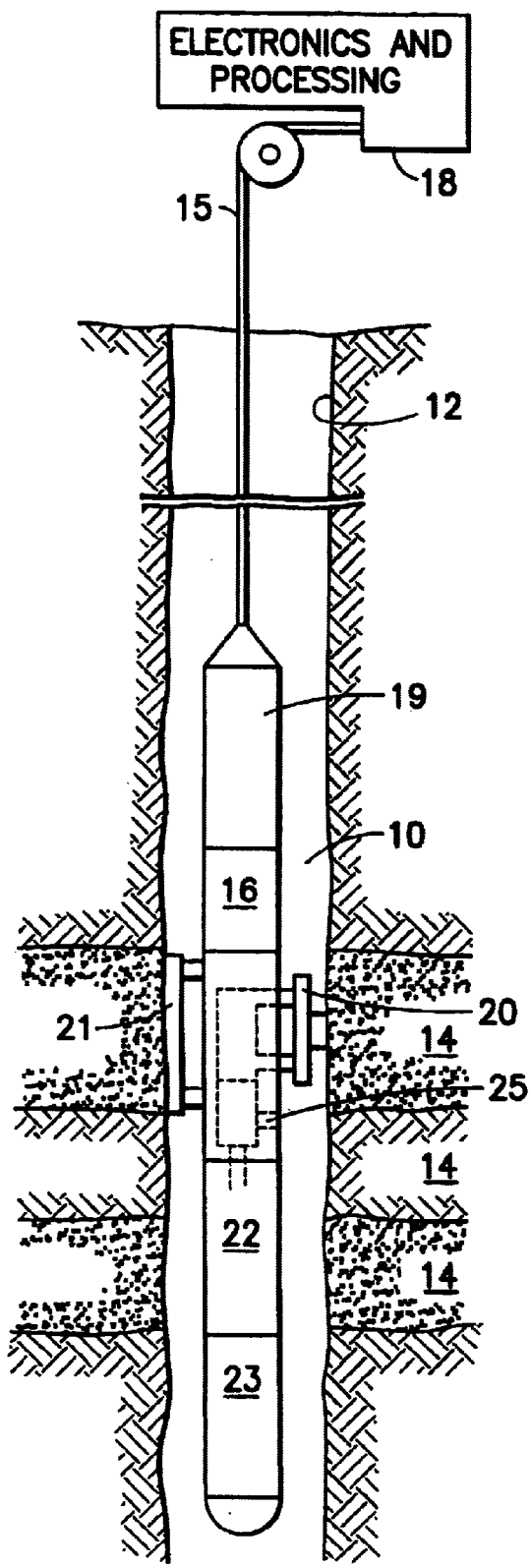
FIG. 1 is a schematic diagram of a borehole apparatus for analyzing formation fluids.

The invention is particularly applicable to both production logging and to borehole investigative logging. For purposes of brevity, however, the description herein will be primarily directed to borehole investigative logging, and the terms "borehole" and "borehole tool" should be read throughout the specification and claims to encompass a (cased) well and a tool used in a well, as well as in a borehole. Thus, a borehole tool 10 for testing earth formations and analyzing the compositions of fluids from the formation 14 in accord with the invention is seen in FIG. 1. As illustrated, the tool 10 is suspended in the borehole 12 from the lower end of a typical multiconductor cable 15 that is spooled in a usual fashion on a suitable winch (not shown) on the formation surface. On the surface, the cable 15 is preferably electrically coupled to an electrical control system 18. The tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the body. The fluid admitting assembly 20 is equipped for selectively sealing off or isolating selected portions of the wall of borehole 12 such that pressure or fluid communication with the adjacent earth formation is established. Also included with tool 10 are a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18.

Additional details of methods and apparatus for obtaining formation fluid samples may be had by reference to U.S. Pat. No. 3,859,851 to Urbanosky, U.S. Pat. No. 3,813,936 to Urbanosky, and U.S. Pat. No. 3,811,321 to Urbanosky, which are hereby incorporated by reference herein. It should be appreciated, however, that it is not intended that the invention be limited to any particular method or apparatus for obtaining the formation fluids.

Figure 2:
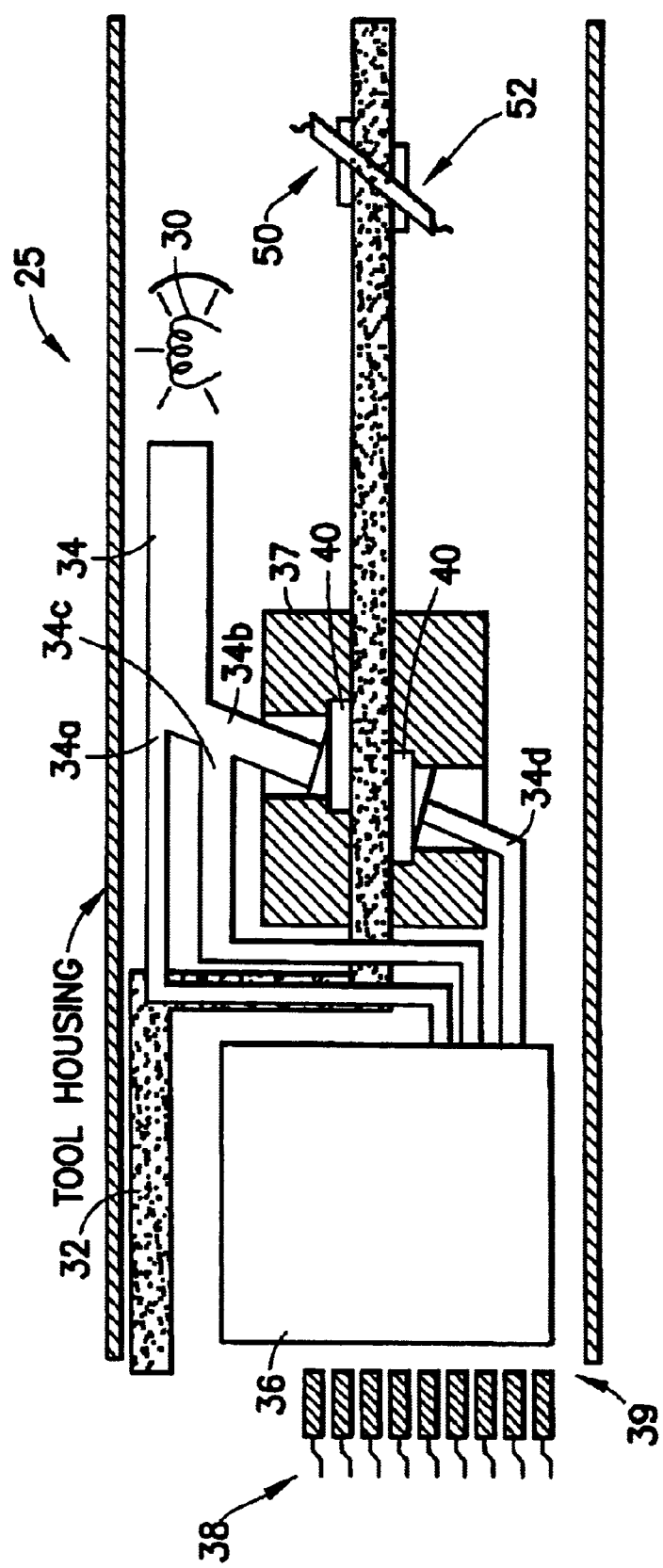
FIG. 2 is a schematic diagram of the optical system of the preferred near infrared fluid analysis module of FIG. 1 for determining fluid compressibility and an apparatus according to the invention for determining speed of sound in fluid.

Turning now to FIG. 2, a preferred fluid analysis module 25 includes a light source 30, a fluid sample tube 32 (coupled to the fluid admitting assembly 20 of FIG. 1), optical fibers 34, and a filter spectrograph 39 which includes a fiber coupler or distributor 36 and an associated detector array 38. The light source 30 is preferably an incandescent tungsten-halogen lamp which is kept at or near atmospheric pressure. The light source 30 is relatively bright throughout the near infrared wavelength region of 1 to 2.5 microns and down to approximately 0.5 microns, and has acceptable emissions from 0.35 to 0.5 microns. Light rays from the light source 30 are preferably transported from the source to the fluid sample by at least part of a fiber optic bundle 34. The fiber optic bundle 34 is preferably split into various sections. A first small section 34a goes directly from the light source 30 to the distributor 36 and is used to sample the light source. A second section 34b is directed into an optical cell 37 through which the sample tube 32 runs and is used to illuminate the fluid sample. A third bundle 34d collects light transmitted or scattered through the fluid sample and provides the filter spectrograph with the light for determining the absorption spectrum of the fluid sample. Optionally, though not necessarily preferred, a fourth fiber optic bundle 34c collects light substantially backscattered from the sample for spectrographic analysis. The backscattered spectrum may be useful if multiple phases are present simultaneously. A three position solenoid (not shown) is used to select which fiber optic bundle is directed toward the filter spectrograph 39. Preferably, a light chopper (not shown) modulates the light directed at the spectrograph at 500 Hz to avoid low frequency noise in the detectors.

As mentioned above, optical bundle 34b directs the light towards the fluid sample. The fluid sample is obtained from the formation by the fluid admitting assembly 20 and is sent to the fluid analysis section 25 in tube 32. The sample tube 32 is preferably a two by six millimeter rectangular channel which includes a section 40 with windows made of sapphire. This window section 40 is located in the optical cell 37 where the light rays are arranged to illuminate the sample. Sapphire is chosen for the windows because it is substantially transparent to the spectrum of the preferred light source and because it is highly resistant to abrasion. As indicated schematically in FIG. 2, the window areas 40 may be relatively thick compared to the rest of the tube 32 to withstand high internal pressure. The fiber optic bundles 34b and 34d are preferably not perpendicular to the window areas 40 so as to avoid specular reflection. The window areas are slightly offset as shown in FIG. 2 to keep them centered in the path of the transmitted light. The signals from the detectors are digitized, multiplexed, and transmitted uphole via the cable 15 to the processing electronics 18 shown in FIG. 1.

Further details regarding the methods and apparatus for optically determining compressibility can be found in the previously incorporated co-owned application. The methods and apparatus provide isothermal compressibility.

According to a presently preferred embodiment of the present invention, a pair of sound (preferably ultrasonic) transceivers 50, 52 are mounted adjacent the tube 32 either upstream or downstream of the optical cell 37. The transceivers 50, 52 are controlled by the uphole electronics 18 via the cable 15 shown in FIG. 1. These devices typically utilize quartz transducers and generate sound pulses in the range of ten micro seconds to one millisecond with a frequency in the range of 100 KHz to one MHz.

The methods of the invention are based on the relationship between density $\rho$, compressibility $\kappa$, and the speed of sound u through a fluid. In the absence of dispersion, the density $\rho$ of a phase of fixed composition is related to the isentropic compressibility $\kappa_s$ and the speed of sound u as defined by Equation (1).

$$\rho = (u^2 \kappa_s)^{-1} \quad (1)$$

Isentropic means that there is constant entropy S, that the process is adiabatic (thermally insulated), and that the process is reversible. The compressibility $\kappa_s$ is defined by Equation (2) where V is volume and p is pressure.

$$\kappa_s = -V^{-1}(\partial V/\partial p)_s \quad (2)$$

An estimate of the plausible error arising from the difference between isothermal compressibility $\kappa_T$ (obtained from the optical measurements described above) and isentropic compressibility $\kappa_s$ (needed to determine density using Equation (1)) can be obtained from the thermodynamic relationship between them given by Equation (3) where $\alpha$ is the isobaric expansivity, and $C_p$ is the heat capacity at constant pressure. $\kappa_T$ is defined by Equation (4) and $\alpha$ is defined by Equation (5).

$$\kappa_T - \kappa_s = T\alpha^2 V/C_p \quad (3)$$

$$k_T = -V^{-1}(\partial V/\partial p)_T \quad (4)$$

$$\alpha = -V^{-1}(\partial V/\partial T)_p \quad (5)$$

In an isolated system of constant energy, volume, and content, the change in entropy over time is given by the relationship (6) where t is time.

$$(\partial S/\partial t)_{U,V,N} > 0 \quad (6)$$

Since $\kappa_T$, T, $\alpha$, V, and $C_p$ are all necessarily positive or zero, it follows that $\kappa_T$ is never less than $\kappa_s$.

Example

For n-octane, at a pressure of 50 MPa and a temperature of 350 K, the following values are obtained from the Equations given above:

$\alpha = 0.00054733$ K$^{-1}$, $\kappa_s = 0.00099997$ MPa$^{-1}$, $\kappa_T = 0.0010594$ MPa$^{-1}$, $C_p = 282.64$ J.mol$^{-1}$.K$^{-1}$, and u=1183.9 m.s$^{-1}$.

Solving Equation (1) using the values u and $\kappa_s$ given above yields a density $\rho = 713.48$ Kg.m$^{-3}$. If the value of $\kappa_T$ is used in Equation (1), rather than the value of $\kappa_s$, the calculated density $\rho = 673.5$ Kg.m$^{-3}$, which is 5.6% lower than the calculated density using $\kappa_s$. It is expected that similar upper bound errors could arise for other hydrocarbons. Thus, even a crude approximation of $\alpha$ and $C_p$ will yield relatively accurate results.

Figure 3:
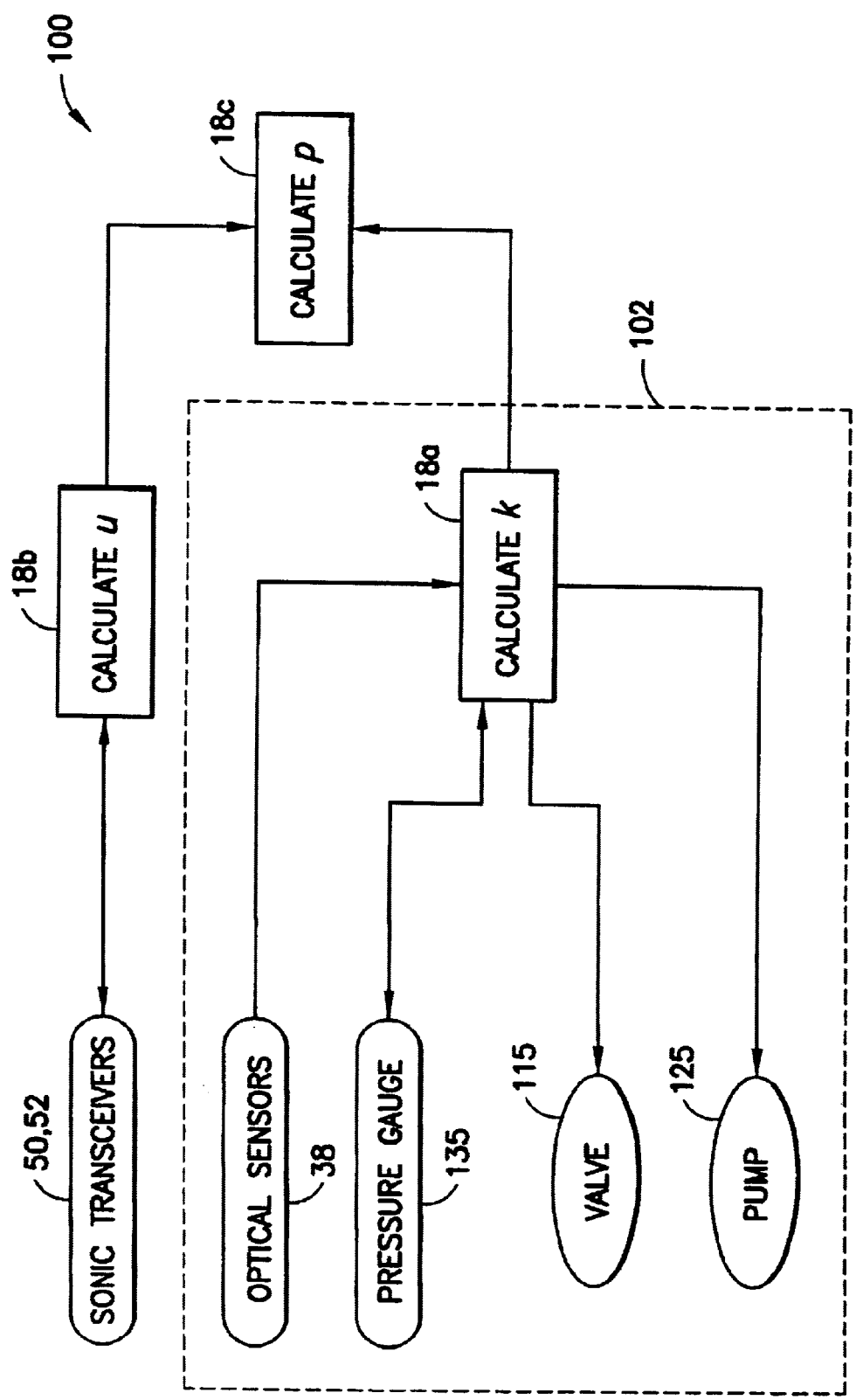
FIG. 3 is a schematic diagram of a system for calculating fluid density according to the invention.

Turning now to FIG. 3, an exemplary system 100 for determining density according to the invention is illustrated in schematic form. The system 100 includes the Optical Fluid Analyzer 102 of the previously incorporated co-owned application. As illustrated in FIG. 3, the reference numerals to the components of the OFA 102 are the same as those used in the previously incorporated co-owned application. These components generally include optical sensors 38, a valve 115, a pump 135, a pressure gauge 135 and processing electronics 18a for calculating the isothermal compressibility $\kappa_T$. The system 100 also includes the aforementioned sonic transceivers 50, 52, processing electronics 18b for calculating the speed of sound u, and processing electronics 18c for calculating density $\rho$. It will be appreciated that the electronics 18a, 18b, and 18c may be a single circuit utilizing one or more microprocessor(s), signal processor(s), and/or application specific integrated circuit(s) ASIC(s)and/ or field programmable gate array(s) FPGA(s).

Figure 4A:
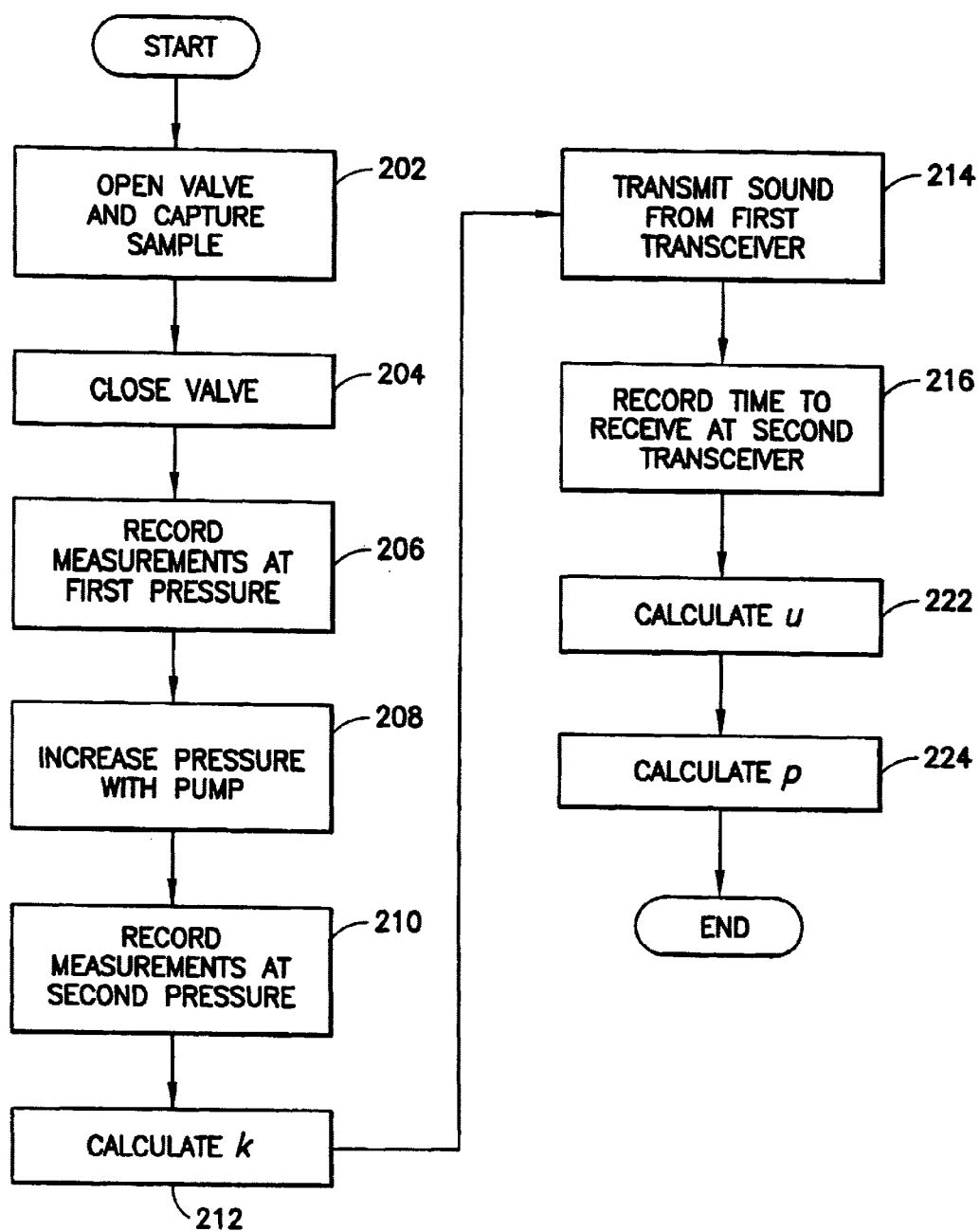
FIGS. 4a and 4b are high level flow charts illustrating the operation of the system of FIG. 3.

Referring now to FIGS. 3 and 4a, the operation of the OFA 102 is as described in the previously incorporated co-owned application which assumes that the fluid sample is stagnant and subject to pressurization. It will be appreciated that in the case of a stagnant sample, only one sonic transceiver and one speed of sound measurement is needed.

In FIG. 4a, the valve 115 is opened and a fluid sample is collected at 202. The valve is closed at 204 and a first measurement is made at 206. The pump 125 is activated to pressure the sample at 208 until a pressure is determined with the pressure gauge 135. A second measurement is made at 210 at the higher pressure. The compressibility is then calculated at 212. As set forth in previously incorporated U.S. Pat. No. 6,474,152, the first and second measurements are optical measurements, which include determinations of the absorption of light at one or more desired wavelengths.

The compressibility of the hydrocarbon fluid is then calculated at 212 based on the optical measurements (in other words, the spectral absorptions) at the two different pressures.

More particularly, for a given hydrocarbon fluid, the magnitude of the absorption will depend upon the pressure of the fluid; the higher the pressure, the greater the absorption. It has been experimentally determined that the change in the absorption that results from a change in pressure correlates directly with fluid compressibility. For pure methane gas, the absorption peak in the 1640–1675 nm range (in other words, the "methane absorption peak") increases from an optical density of approximately 0.3 to an optical density of nearly 0.7 as pressure is increased from 2 kpsi to 20 kpsi. By integrating the area under each of the optical density curves, "peak areas" (in other words, the area under the optical density peak) can be found. The optically determined peaks areas of methane at different temperature have a linear relationship with the mass density of the methane at those temperatures. Likewise, the optically determined peak areas of a methane/heptane hydrocarbon mixture have a linear relationship with the mass density of the mixture at different temperatures. It will be appreciated that the slope of the line defining the linear relationship between peak areas and mass density is specific to the hydrocarbon fluid or fluid mixture being analyzed.

Given the above, a relative change in fluid volume (due to a change in pressure) can be related to a change in density according to $$\partial V/V = -\partial\rho/\rho \quad (7)$$

where V is the volume and $\rho$ is the density of the fluid. Since there is a linear relationship between the density $\rho$ and the peak area $\psi$; in other words, $\psi = m\rho$ where m is a constant, it follows that $$\partial\psi = m\partial\rho \quad (8)$$

Therefore, using equations (7) and (8) and the definition of fluid compressibility $\beta$, it can be shown that $$\beta = \frac{1}{\Psi}\left(\frac{\partial\Psi}{\partial P}\right)_T \quad (9)$$

where $\beta$ is the fluid compressibility, $\partial\psi$ is the difference in peak areas, $\partial P$ is the difference in pressure, and the peak area $\psi$ is a variable which changes as the pressure changes. It is noted that equation (9) can be estimated according to:

$$\beta = \frac{1}{\Psi}\left(\frac{\Delta\Psi}{\Delta P}\right)_T \quad (10)$$

where $\psi$ is preferably the initial peak area, and $\Delta\psi = \partial\psi$ an $\Delta P = \partial P$. From equations (9) and (10), it is evident that at any given temperature, fluid compressibility can be determined from the change in the peak area (due to the change in pressure) divided by the change in pressure, and the peak area itself. The change in pressure is measured by the pressure gauge 135, while the change in peak area is measured by the optical sensors. It is noted that the peak area determination for a particular sensor is determined from the raw data count of the sensor; in other words, the peak area is the optical density for the wavelength width of that channel. Thus, optical sensors at wavelengths corresponding to peak areas of hydrocarbon fluids which are likely to be encountered in the formation are utilized; for example, at and/or around 6,000 cm$^{-1}$ and 5,800 cm$^{-1}$ (the absorption peaks of methane and crude oil respectively).

In sum, in order to determine compressibility, an OFA-type tool is used to subject formation fluids to NIR illumination and to provide spectral absorption measurements of peaks at and/or around about 6,000 cm$^{-1}$ and about 5,800 cm$^{-1}$ (the absorption peaks of methane and crude oil respectively). The spectral absorptions are measured at two different pressures, and the compressibility of the fluid is determined from the change in the peak areas, the change in pressure, and the peak area itself.

Returning now to FIG. 4a, using the sonic transceivers 50, 52, a sound is transmitted from one to the other at 214 and the transit time $t_1$ of the sound is recorded at 216. If desired, a sound may also be transmitted from the second transceiver to the first at 218 with a second transit time $t_2$ being recorded at 220. The transit time(s), taken in conjunction with the know distance between the transceivers yield a velocity at 222.

Having calculated the compressibility of the sample at 212 and the speed of sound through the sample at 222, the density is then calculated at 224 and the process ends at 226. Those skilled in the art will appreciate that the density calculation can be performed using the isothermal compressibility obtained at 212 or, for a more accurate calculation, the isentropic compressibility can be obtained from the isothermal compressibility using estimates of $C_p$ and $\alpha$ as described above. It will also be appreciated that the operation of the OFA at 202 through 212 may be performed after the calculation of the speed of sound at 222 rather than before the operation of the first transceiver at 214. It will also be understood that, depending on the apparatus used, it is possible to perform the optical and sonic operations simultaneously.

Figure 4B:
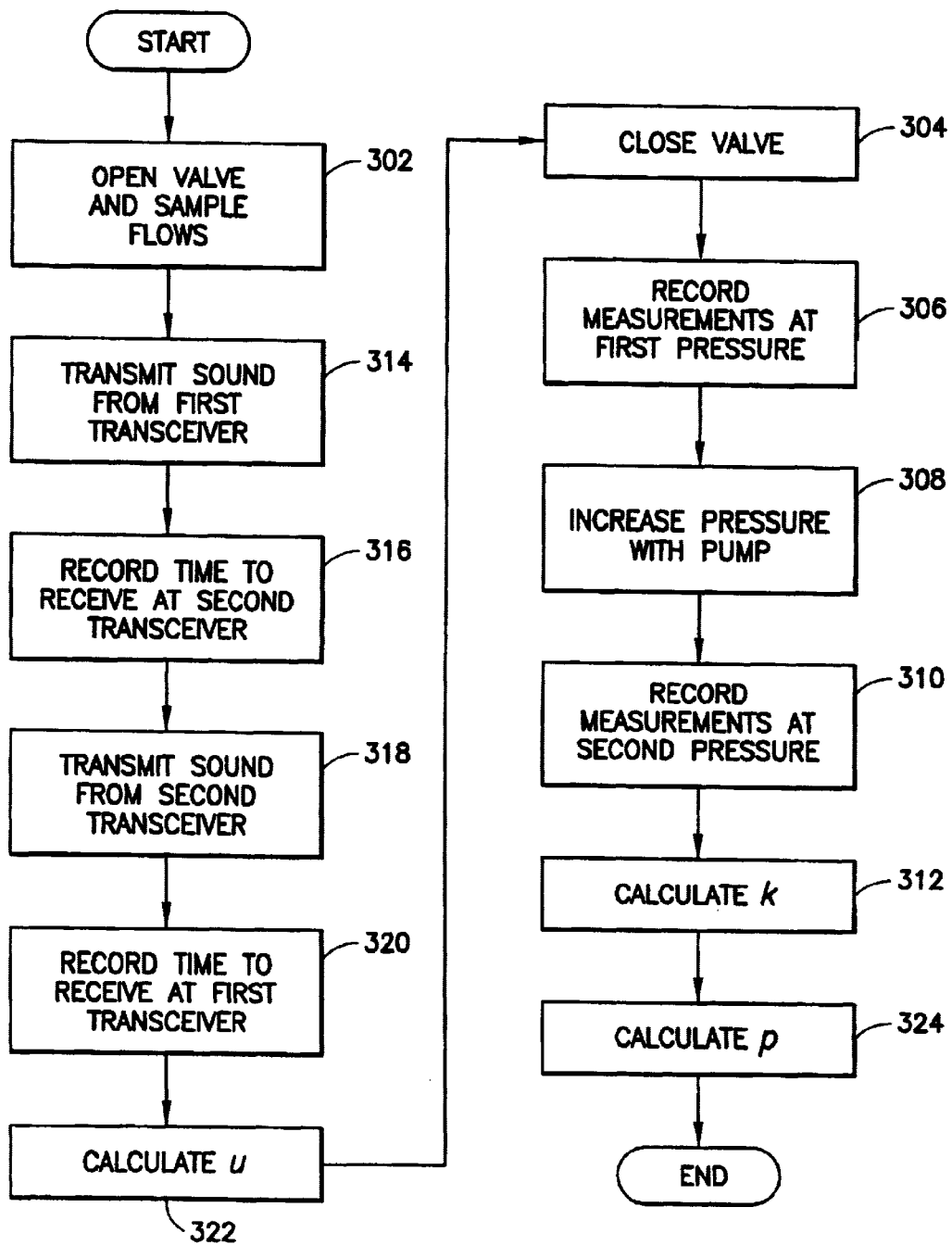

Turning now to FIG. 4b, according to an alternate embodiment, the sonic measurements are made on flowing fluid before the optical measurements are made on stagnant fluid. Accordingly, after the valve is opened at 302, two sonic measurements are made on the flowing fluid before the valve is closed at 304. In particular, as seen in FIG. 4b, sound is transmitted at 314 from the first transceiver to the second transceiver and the first time is recorded at 316. Sound is then sent from the second transceiver to the first transceiver at 318 and the second time is recorded at 320. The first time and the second time, taken in conjunction with the known distance between the transceivers yield two velocities. Those skilled in the art will appreciate that one of the velocities represents the speed of sound through the fluid plus the velocity of the fluid and the other represents the speed of sound through the fluid minus the velocity of the fluid. Thus, the sum of the two velocities will equal two times the speed of sound through the fluid and the difference between the velocities will equal two times the flow rate of the fluid. Thus, at 322 is possible to calculate both the speed of sound through the fluid and the flow rate of the sample.

After the valve is closed at 304, the OFA is operated at 306–312 in the manner described in the previously incorporated co-owned application to determine compressibility at 312. Having calculated the speed of sound through the sample at 322 and the compressibility of the sample at 312, the density is then calculated at 324 using Equation (1).

There have been described and illustrated herein several embodiments of methods and apparatus for determining the density of a downhole fluid. While particular embodiments of the invention have been described, it is not intended that the invention be limited thereto, as it is intended that the invention be as broad in scope as the art will allow and that the specification be read likewise. Thus, while specific apparatus have been disclosed, it will be appreciated that other apparatus for determining compressibility and speed of sound through the fluid could be utilized. Also, while two sonic transceivers have been shown, it will be recalled that in the case of a stagnant sample a single transceiver is sufficient. It will therefore be appreciated by those skilled in the art that yet other modifications could be made to the provided invention without deviating from its spirit and scope as so claimed.

What is claimed is:

1. A method for determining the density of hydrocarbon fluid in a formation, comprising:
   a) obtaining a sample of the hydrocarbon fluid from the formation;
   b) determining the compressibility of the sample;
   c) determining the speed of sound trough the sample; and
   d) calculating the density of the sample from the compressibility and the speed of sound through the sample.

2. The method according to claim 1, wherein:
said determining the compressibility of the sample is performed by obtaining an isothermal compressibility with optical fluid analysis and by approximating the compressibility using said isothermal compressibility.

3. The method according to claim 1, wherein:
said determining the speed of sound through the sample is performed with a sonic transceiver.

4. The method according to claim 3, wherein:
said determining the speed of sound through the sample is performed with two sonic transceivers.

5. The method according to claim 3, wherein:
said determining the speed of sound through the sample is performed with a time of flight flow meter.

6. The method according to claim 1, wherein:
said determining compressibility includes determining the isentropic compressibility of the sample, and
said calculating density is based on the relationship $$\rho = (u^2 \kappa_s)^{-1}$$

where $\rho$ is density, u is the speed of sound through the medium and $\kappa_s$ is the isentropic compressibility of the sample.

7. The method according to claim 1, wherein:
said determining compressibility includes determining the isothermal compressibility of the sample and approximating said compressibility from the isothermal compressibility, and
said calculating density is based on the relationship $$\kappa = (u^2 \kappa_T)^{-1}$$

where $\rho$ is density, u is the speed of sound through the medium and $\kappa_T$ is the isothermal compressibility of the sample.

8. An apparatus for determining the density of hydrocarbon fluid in a formation, comprising:
   a) fluid conduit which receives a sample of the hydrocarbon fluid from the formation;
   b) means for determining the compressibility of the sample;
   c) means for determining the speed of sound through the sample; and
   d) means for calculating the density of the sample from the compressibility and the speed of sound through the sample.

9. The apparatus according to claim 8, wherein:
said means for determining the compressibility of the sample includes means for finding isothermal compressibility of the sample using an optical fluid analyzer, wherein said compressibility is approximated from said isothermal compressibility.

10. The apparatus according to claim 8, wherein:
said means for determining the speed of sound through the sample includes a sonic transceiver.

11. The apparatus according to claim 10, wherein:
said means for determining the speed of sound through the sample includes two sonic transceivers.

12. The apparatus according to claim 10, wherein:
said means for determining the speed of sound through the sample includes a time of flight flow meter.

13. The apparatus according to claim 8, wherein:
said means for determining compressibility includes means for determining the isentropic compressibility of the sample, and
said means for calculating density utilizes the relationship $$\rho = (u^2 \kappa_s)^{-1}$$

where $\rho$ is density, u is the speed of sound through the medium and $\kappa_s$ is the isentropic compressibility of the sample.

14. The apparatus according to claim 8, wherein:
said means for determining compressibility includes means for determining the isothermal compressibility of the sample and for approximating said compressibility from said isothermal compressibility, and
said means for calculating density is based on the relationship $$\rho = (u^2 \kappa_T)^{-1}$$

where $\rho$ is density, u is the speed of sound through the medium and $\kappa_T$ is the isothermal compressibility of the sample.

15. The method according to claim 2, wherein:
said approximating the compressibility using said isothermal compressibility comprises estimating compressibility according to $\kappa_T - \kappa_s = T\alpha^2 V/C_p$ where $\kappa_s$ said compressibility, $\kappa_T$ is said isothermal compressibility, T is temperature, V is volume, $\alpha$ is the isobaric expansivity, and $C_p$ is the heat capacity at constant pressure, and $\kappa_T = -V^{-1}(\partial V/\partial p)_T$ and $\alpha = -V^{-1}(\partial V/\partial T)_p$ where p is pressure.

16. The method according to claim 7, wherein:
said approximating the compressibility using said isothermal compressibility comprises estimating compressibility according to $\kappa_T - \kappa_s = T\alpha^2 V/C_p$ where $\kappa_s$ is said compressibility, $\kappa_T$ is said isothermal compressibility, T is temperature, V is volume, $\alpha$ is the isobaric expansivity, and $C_p$ is the heat capacity at constant pressure, and $\kappa_T = -V^{-1}(\partial V/\partial p)_T$ and $\alpha = -V^{-1}(\partial V/\partial T)_p$ where p is pressure.

17. The apparatus according to claim 9, wherein: said compressibility is approximated according to $\kappa_T - \kappa_s = T\alpha^2 V/C_p$ where $\kappa_s$ is said compressibility, $\kappa_T$ is said isothermal compressibility, T is temperature, V is volume, $\alpha$ is the isobaric expansivity, and $C_p$ is the heat capacity at constant pressure, and $\kappa_T = -V^{-1}(\partial V/\partial p)_T$ and $\alpha = -V^{-1}(\partial V/\partial T)_p$ where p is pressure.

18. The apparatus according to claim 14, wherein:
said compressibility is approximated according to $\kappa_T - \kappa_s = T\alpha^2 V/C_p$ where $\kappa_s$ is said compressibility, $\kappa_T$ is said isothermal compressibility, T is temperature, V is volume, $\alpha$ is the isobaric expansivity, and $C_p$ is the heat capacity at constant pressure, and $\kappa_T = -V^{-1}(\partial V/\partial p)_T$ and $\alpha = -V^{-1}(\partial V/\partial T)_p$ where p is pressure.

* * * * *